(12) United States Patent
Steed et al.

(10) Patent No.: US 12,017,003 B2
(45) Date of Patent: Jun. 25, 2024

(54) CUSHION MEMBER AND METHOD OF MANUFACTURING SAME

(71) Applicant: KONINKLIJKE PHILIPS N.V., Eindhoven (NL)

(72) Inventors: Daniel Steed, North Huntingdon, PA (US); Richard Thomas Haibach, Verona, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1416 days.

(21) Appl. No.: 16/465,328

(22) PCT Filed: Dec. 5, 2017

(86) PCT No.: PCT/EP2017/081440
§ 371 (c)(1),
(2) Date: May 30, 2019

(87) PCT Pub. No.: WO2018/104259
PCT Pub. Date: Jun. 14, 2018

(65) Prior Publication Data
US 2019/0388636 A1 Dec. 26, 2019

Related U.S. Application Data

(60) Provisional application No. 62/431,529, filed on Dec. 8, 2016.

(51) Int. Cl.
*A61M 16/06* (2006.01)

(52) U.S. Cl.
CPC . *A61M 16/0605* (2014.02); *A61M 2016/0661* (2013.01); *A61M 2205/0227* (2013.01); *A61M 2210/0618* (2013.01)

(58) Field of Classification Search
CPC .............. A61M 16/06; A61M 16/0666; A61M 16/0605; A61M 2016/0661
See application file for complete search history.

(56) References Cited

U.S. PATENT DOCUMENTS

| 6,712,072 B1 | 3/2004 | Lang |
| 10,610,657 B2 | 4/2020 | Eury |

(Continued)

FOREIGN PATENT DOCUMENTS

| WO | WO2013056389 A1 | 4/2013 |
| WO | 2016050814 A | 4/2016 |

OTHER PUBLICATIONS

PCT International Search Report, International application No. PCT/EP2017/081440, dated Feb. 21, 2018.

*Primary Examiner* — Colin W Stuart
*Assistant Examiner* — Douglas Y Sul
(74) *Attorney, Agent, or Firm* — Michael W. Haas

(57) ABSTRACT

A cushion member (2) is for a patient interface device. The cushion member includes a body portion (4) having a first end (6) and a second end (8) disposed opposite the first end, the body portion defining a passage (5) therethrough, and a support portion (10) extending from the second end into the passage. The support portion includes a first portion (12) and a second portion (14) disposed on or in the first portion. The support portion is movable from a first configuration to a second configuration responsive to a change in environment.

13 Claims, 3 Drawing Sheets

(56) References Cited

U.S. PATENT DOCUMENTS

| | | | |
|---|---|---|---|
| 2008/0289633 A1* | 11/2008 | Kwok | A61M 16/0825 128/206.24 |
| 2010/0024811 A1* | 2/2010 | Henry | A61M 16/0622 128/202.16 |
| 2011/0088698 A1 | 4/2011 | Barnett | |
| 2014/0196720 A1 | 7/2014 | Eury | |
| 2014/0326243 A1 | 11/2014 | Znamenskiy | |
| 2015/0209540 A1* | 7/2015 | Hendriks | A61M 16/0683 128/205.25 |
| 2017/0007861 A1* | 1/2017 | Parham | A62B 18/025 |
| 2017/0361045 A1 | 12/2017 | Fu | |

* cited by examiner

CUSHION MEMBER AND METHOD OF MANUFACTURING SAME

CROSS-REFERENCE TO RELATED APPLICATIONS

This patent application claims the priority benefit under 35 U.S.C. § 371 of international patent application no. PCT/EP2017/081440, filed Dec. 5, 2017, which claims the priority benefit under 35 U.S.C. § 119(e) of U.S. Provisional Patent Application No. 62/431,529, filed on Dec. 8, 2016, the contents of which are herein incorporated by reference.

BACKGROUND OF THE INVENTION

1. Field of the Invention

The present invention relates to cushion members such as, for example, cushion members for patient interface devices. The present invention also relates to methods of manufacturing cushion members.

2. Description of the Related Art

Many individuals suffer from disordered breathing during sleep. Sleep apnea is a common example of such sleep disordered breathing suffered by millions of people throughout the world. One type of sleep apnea is obstructive sleep apnea (OSA), which is a condition in which sleep is repeatedly interrupted by an inability to breathe due to an obstruction of the airway; typically the upper airway or pharyngeal area. Obstruction of the airway is generally believed to be due, at least in part, to a general relaxation of the muscles which stabilize the upper airway segment, thereby allowing the tissues to collapse the airway. Another type of sleep apnea syndrome is a central apnea, which is a cessation of respiration due to the absence of respiratory signals from the brain's respiratory center. An apnea condition, whether obstructive, central, or mixed, which is a combination of obstructive and central, is defined as the complete or near cessation of breathing, for example a 90% or greater reduction in peak respiratory air-flow.

Those afflicted with sleep apnea experience sleep fragmentation and complete or nearly complete cessation of ventilation intermittently during sleep with potentially severe degrees of oxyhemoglobin desaturation. These symptoms may be translated clinically into extreme daytime sleepiness, cardiac arrhythmias, pulmonary-artery hypertension, congestive heart failure and/or cognitive dysfunction. Other consequences of sleep apnea include right ventricular dysfunction, carbon dioxide retention during wakefulness, as well as during sleep, and continuous reduced arterial oxygen tension. Sleep apnea sufferers may be at risk for excessive mortality from these factors as well as by an elevated risk for accidents while driving and/or operating potentially dangerous equipment.

Even if a patient does not suffer from a complete or nearly complete obstruction of the airway, it is also known that adverse effects, such as arousals from sleep, can occur where there is only a partial obstruction of the airway. Partial obstruction of the airway typically results in shallow breathing referred to as a hypopnea. A hypopnea is typically defined as a 50% or greater reduction in the peak respiratory air-flow. Other types of sleep disordered breathing include, without limitation, upper airway resistance syndrome (UARS) and vibration of the airway, such as vibration of the pharyngeal wall, commonly referred to as snoring.

It is well known to treat sleep disordered breathing by applying a continuous positive air pressure (CPAP) to the patient's airway. This positive pressure effectively "splints" the airway, thereby maintaining an open passage to the lungs. It is also known to provide a positive pressure therapy in which the pressure of gas delivered to the patient varies with the patient's breathing cycle, or varies with the patient's breathing effort, to increase the comfort to the patient. This pressure support technique is referred to as bi-level pressure support, in which the inspiratory positive airway pressure (IPAP) delivered to the patient is higher than the expiratory positive airway pressure (EPAP). It is further known to provide a positive pressure therapy in which the pressure is automatically adjusted based on the detected conditions of the patient, such as whether the patient is experiencing an apnea and/or hypopnea. This pressure support technique is referred to as an auto-titration type of pressure support, because the pressure support device seeks to provide a pressure to the patient that is only as high as necessary to treat the disordered breathing.

Pressure support therapies as just described involve the placement of a patient interface device including a mask component having a soft, flexible sealing cushion on the face of the patient. The mask component may be, without limitation, a nasal mask that covers the patient's nose, a nasal/oral mask that covers the patient's nose and mouth, or a full face mask that covers the patient's face. Such patient interface devices may also employ other patient contacting components, such as forehead supports, cheek pads and chin pads. The patient interface device is typically secured to the patient's head by a headgear component. The patient interface device is connected to a gas delivery tube or conduit and interfaces the pressure support device with the airway of the patient, so that a flow of breathing gas can be delivered from the pressure/flow generating device to the airway of the patient.

One drawback of known patient interface devices is that during therapy, leaks often form between the sealing portion of the cushion and the patient's face. Leaks cause rushes of gas flow against the patient's skin, which can prevent a patient from remaining asleep and also compromise the quality of therapy being delivered to the patient.

SUMMARY OF THE INVENTION

Accordingly, it is an object of the present invention to provide an improved cushion member and method of manufacturing the same.

In accordance with one aspect of the disclosed concept, a cushion member is provided for a patient interface device. The cushion member includes a body portion having a first end and a second end located opposite the first end, the body portion defining a passage therethrough; and a support portion extending from the second end into the passage. The support portion includes a first portion and a second portion located on the first portion. The support portion is movable from a first configuration to a second configuration responsive to a change in environment. The support portion changes shape when moving from the first configuration to the second configuration.

In accordance with another aspect of the disclosed concept, a method of manufacturing a cushion member for a patient interface device is provided. The method includes the steps of providing a body portion having a first end and a second end located opposite the first end, the body portion defining a passage therethrough; providing a first portion of a support portion, the first portion extending from the second end into the passage; and providing a second portion of the support portion on the first portion. The support portion is movable from a first configuration to a second configuration responsive to a change in environment. The support portion changes shape when moving from the first configuration to the second configuration.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "fixedly coupled" or "fixed" means that two components are coupled so as to move as one while maintaining a constant orientation relative to each other.

As employed herein, the statement that two or more parts or components "engage" one another shall mean that the parts exert a force against one another either directly or through one or more intermediate parts or components. As used herein, "directly engage" means that two elements are directly in contact with each other and exert a force against each other. As employed herein, the term "number" shall mean one or an integer greater than one (i.e., a plurality).

As used herein, the phrase "chemical bond" shall mean a bond formed as a result of the curing (i.e., solidifying) of a first material to a second material. In one non-limiting example, the first and second materials are each made of a monomer, a polymer, or a mixture of a monomer and a polymer.

As employed herein, the term "configuration" shall mean a geometric profile not limited by scale or sizing. As employed herein, a component having a geometric profile that increases or decreases in scale or size does not change configuration, whereas a component whose geometric profile changes undergoes a change in configuration.

As employed herein, the term "predetermined" shall mean intentional and preplanned. For example and without limitation, movement of a support portion in an intentional and preplanned manner is movement in a predetermined manner, whereas incidental, unplanned, and/or unintended movement of a support portion is not movement in a predetermined manner.

Figure 1:
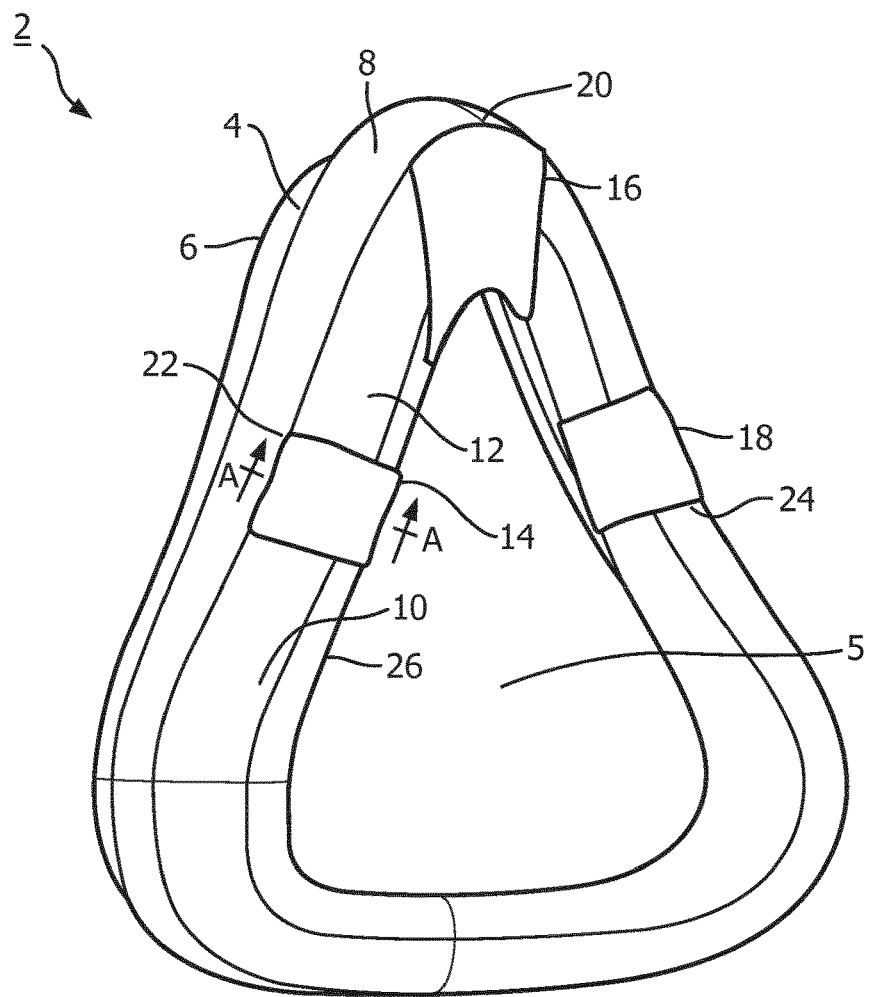
FIG. 1 is an isometric view of the user facing side of a cushion member, in accordance with a non-limiting embodiment of the disclosed concept.

FIG. 1 shows an isometric view of a cushion member 2, in accordance with one non-limiting embodiment of the disclosed concept. Cushion member 2 may be employed in a suitable patient interface device and be secured to the face of a patient in order to allow pressure support therapy to be delivered to the patient. Cushion member 2 includes a body portion 4 and a support portion (e.g., without limitation, sealing portion 10) extending from body portion 4. Body portion 4 includes a first end 6 and a second end 8 located opposite first end 6. As shown, body portion 4 defines a passage 5 therethrough and sealing portion 10 extends radially inwardly from second end 8 into passage 5. As a result, breathing gas is able to be passed through body portion 4 and sealing portion 10 to the patient.

Sealing portion 10 includes a first portion 12 and a number of other portions (e.g., without limitation, second, third, and fourth portions 14, 16, 18) located on first portion 12 and facing away from an interior of body portion 4. First portion 12 includes a nose bridge region 20, a first cheek region 22, and a second cheek region 24 located opposite first cheek region 22. Each of regions 20, 22, 24 are positioned so as to engage, respectively, at or about the nose bridge, left cheek, and right cheek regions of a patient. Second portion 14 is located on first cheek region 22, third portion 16 is located on nose bridge region 20, and fourth portion 18 is located on second cheek region 24.

First portion 12 is made of a first material and second, third, and fourth portions 14, 16, 18 are made of a second material different than first material, and are disposed on the first material. The second material of second, third, and fourth portions 14, 16, 18 has a coefficient of thermal expansion and the first material of first portion 12 has a coefficient of thermal expansion different than, and in one embodiment less than, the coefficient of thermal expansion of the second material. Additionally, in one embodiment the difference between the coefficients of thermal expansion of the first and second materials is a first number, the average of the coefficients of thermal expansion of the first and second materials is a second number, and the first number divided by the second number is greater than 0.10.

Sealing portion 10 is structured to move from a first configuration (FIG. 2) to a second configuration (FIG. 3) responsive to a change in environment. In one non-limiting embodiment, the change in environment is a change in temperature. In another non-limiting embodiment, the change in environment is a change in humidity. In one embodiment, the two different materials are both silicone and are each chemically bonded to one another. Changes in temperature or humidity may occur, for example and without limitation, when pressure support therapy is being delivered to a patient, sealing portion 10 engages the face of the patient, and leaks occur between the face of the patient and sealing portion 10. That is, gusts of relatively moist and/or hot gas pass over sealing portion 10 when there is a leak.

In such a situation, the material of second, third, and fourth portions 14, 16, 18 will expand more than the material of first portion 12 due to its relatively large coefficient of thermal expansion. As a result, sealing portion 10 will change shape, morph, or otherwise deform such that it becomes more outwardly convex, and thus better concentrates sealing forces against the face of the patient. That is, when environmental conditions cause sealing portion 10 to change (i.e., due to gas flow or moisture flow between sealing portion 10 and the face of the patient), sealing portion 10 will change shape and provide an improved seal against the face of the patient. Such arrangement is different from prior art sealing portions (not shown), which are made of one single material, and as such, expand or contract uniformly such that a planar geometric sealing portion will remain a planar geometric sealing portion responsive to a change in environment (i.e., no change in shape). Thus, the dual material sealing portion 10, by virtue of having two separate materials with separate coefficients of thermal expansion, is able to move to a more seal-friendly configuration wherein contact area with the face of the user is decreased, thereby increasing the pressure between sealing portion 10 and the face of the user. It follows that the potential for leaks is significantly minimized when cushion member 2 is donned, thereby improving the ability of the patient to remain asleep and thus the quality of pressure support therapy being delivered.

Figure 2:
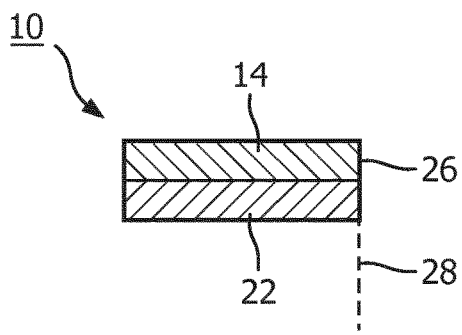
FIG. 2 is a section view of a support portion of the cushion member of FIG. 1, taken along line A-A of FIG. 1, and shown in a first configuration.
Figure 3:
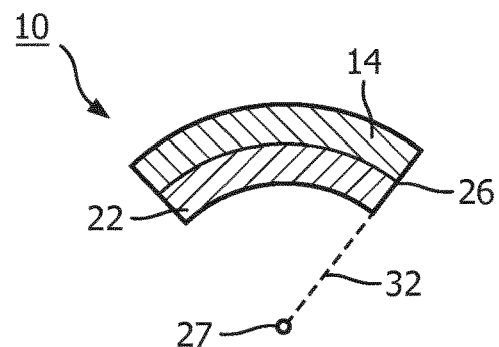
FIG. 3 is another section view of the support portion of FIG. 2, shown in a second configuration.

FIG. 2 shows a section view of sealing portion 10 in the first configuration and FIG. 3 shows a section view of sealing portion 10 in the second configuration. As shown, the shape of sealing portion 10 changes when sealing portion 10 moves from the first configuration (FIG. 2) to the second configuration (FIG. 3), the causation of which is discussed hereinabove. More specifically, the curvature changes such that sealing portion 10 is more outwardly convex in the second configuration (FIG. 3) than the first configuration (FIG. 2). As shown in FIG. 1, sealing portion 10 has an inner edge portion 26 located inboard of second end 8 of body portion 4. Cushion member 2 has a first center of curvature (not shown in FIG. 2 because sealing portion 10 is relatively flat in the first configuration) when sealing portion 10 is in the first configuration and a first radius of curvature 28 (partially shown) extending from the first center of curvature to inner edge portion 26. Cushion member has a second center of curvature 27 (FIG. 3) when sealing portion 10 is in the second configuration and a second radius of curvature 32 extending from second center of curvature 27 to inner edge portion 26. Second center of curvature 27 is closer to sealing portion 10 than the first center of curvature. Second radius of curvature 32 is less than first radius of curvature 28. It will be appreciated that when sealing portion 10 moves from the first configuration to the second configuration, sealing portion 10 moves in a predetermined manner in order to be more curved. That is, sealing portion 10 purposefully changes shape in order to be more outwardly convex, and thus provide an improved seal.

In the exemplary embodiment of FIG. 1, second, third, and fourth portions 14, 16, 18 substantially overlay first cheek, nose bridge, and second cheek regions, respectively, when cushion member 2 is engaged with the face of a patient. These are locations where leaks between sealing portions and the face of the patient commonly occur. However, it will be appreciated that a second material may be located on any location and in any configuration on a first portion being made of a different first material, without departing from the scope of disclosed concept. Additionally, as discussed herein, support portion 10 is a sealing portion 10 structured to directly engage the face of a user. However, it will be appreciated that the disclosed dual material concept may be employed with, for example and without limitation, another support portion that extends into passage 5, but that is positioned between sealing portion 10 and first end 6 and is structured to directly support and engage sealing portion 10 (e.g., without limitation, a support which underlies a sealing flap which directly engages the face of a patient).

Figure 4:
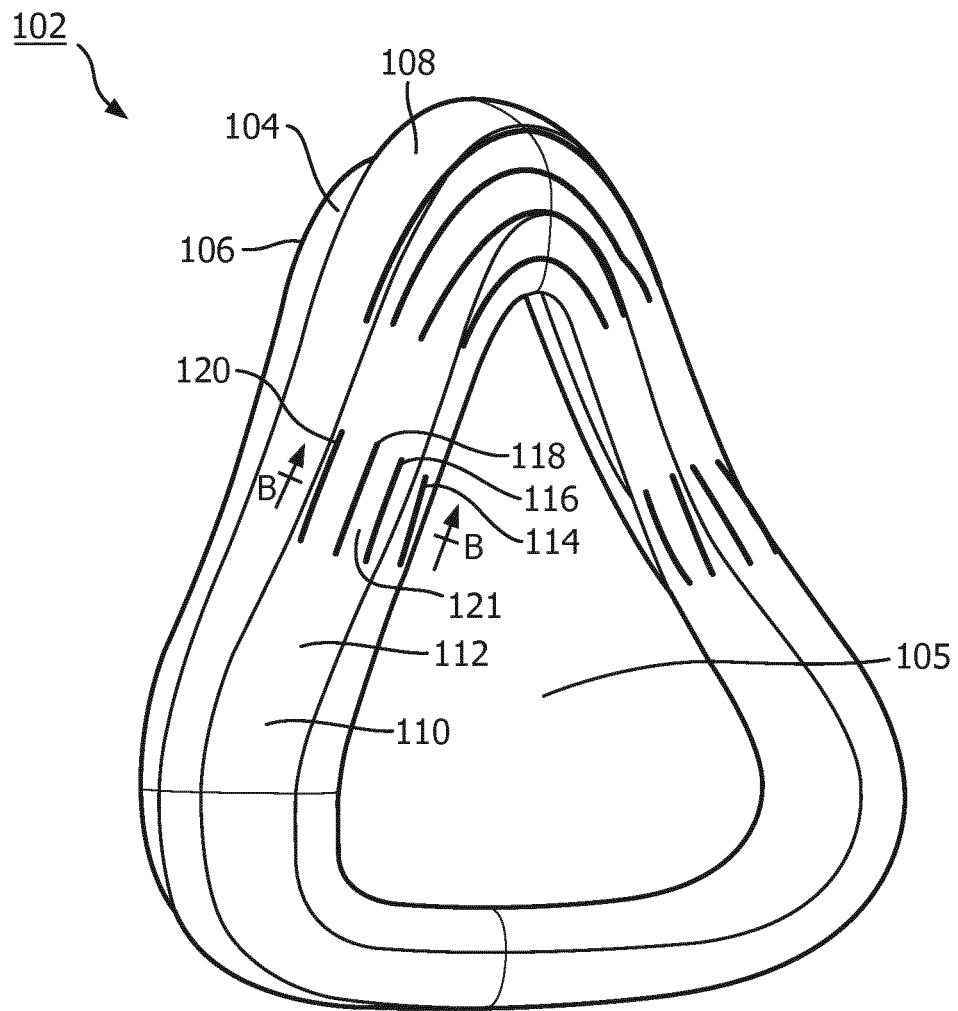
FIG. 4 is an isometric view of the user facing side of another cushion member, in accordance with another non-limiting embodiment of the disclosed concept.

FIG. 4 shows an isometric view of another cushion member 102, in accordance with another non-limiting embodiment of the disclosed concept. Cushion member 102 has a body portion 104 having opposing ends 106, 108, and a support portion (e.g., without limitation, sealing portion 110) extending from second end 108 into a passage 105 defined by body portion 104. As shown, sealing portion 110 has a first portion 112 and a number of other portions 114, 116, 118, 120 located on first portion 112. For economy of disclosure, only portions 114, 116, 118, 120 located on a cheek region of first portion 112 will be discussed in detail, although it will be appreciated that sealing portion 110 has a number of other portions located on nose bridge region of first portion 112 and the corresponding opposing cheek region of first portion 112.

Figure 5:
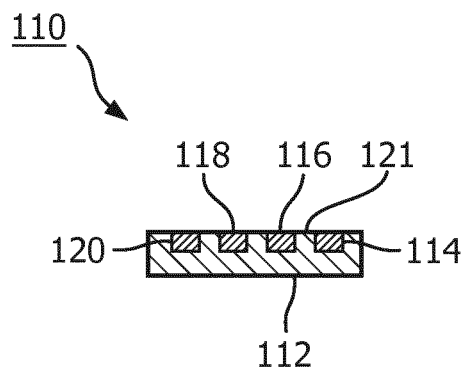
FIG. 5 is a section view of a support portion of the cushion member of FIG. 4, taken along line B-B of FIG. 4, and shown in a first configuration.
Figure 6:
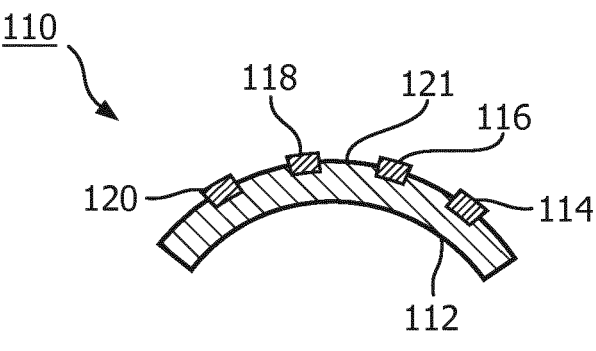
FIG. 6 is another section view of the support portion of FIG. 5, shown in a second configuration.

FIG. 5 shows sealing portion 110 in a first configuration and FIG. 6 shows sealing portion 110 in a second configuration. It will be appreciated that sealing portion 110 changes shape (i.e., becomes more convex and/or has a reduced radius of curvature) when moving from the first configuration (FIG. 5) to the second configuration (FIG. 6) responsive to a change in environment (e.g., without limitation, temperature and/or humidity), thereby providing substantially the same improved sealing advantages as sealing portion 10 (FIGS. 1-3), discussed above. However, as shown in FIGS. 5 and 6, portions 114, 116, 118, 120 partially extend into first portion 112, rather than primarily overlaying first portion 112, as is the case with portions 14, 16, 18 and portion 12. As a result, sealing portion 110 is advantageously able to provide a roughened, multifaceted sealing surface. More specifically, sealing portion 110 further has an engaging portion 121 structured to engage the face of a user. Engaging portion 121 faces away from an interior of body portion 104. When sealing portion 110 is in the first configuration (FIG. 5), engaging portion 121 is generally smooth. When sealing portion 110 is in the second configuration (FIG. 6), engaging portion 121 is roughened such that portions 114, 116, 118, 120 extend outwardly from an interior of first portion 112.

It will however be appreciated that a similar suitable alternative sealing portion (not shown) could have second portions inset from a first portion in a first configuration such that in a second configuration the first and second portions would be smooth, and not roughened. Additionally, although support portion 110 has been described as a sealing portion 110, it will be appreciated that the disclosed dual material concept may be employed with, for example and without limitation, another support portion that extends into passage 105, but that is positioned between sealing portion 110 and first end 106 and is structured to directly support and engage sealing portion 110 (e.g., without limitation, a support which underlies a sealing flap which directly engages the face of a patient).

Figure 7:
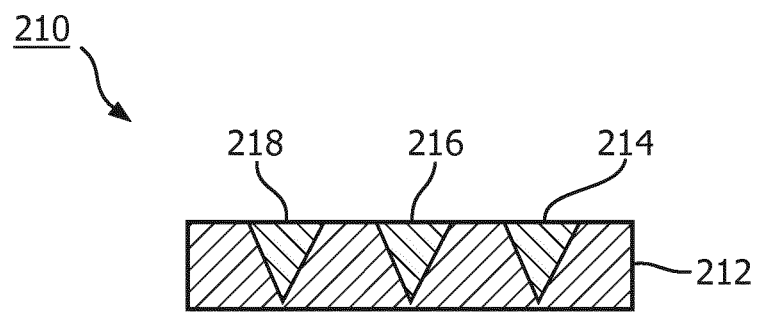
FIG. 7 is a section view of another support portion, shown in a first configuration, in accordance with another non-limiting embodiment of the disclosed concept.
Figure 8:
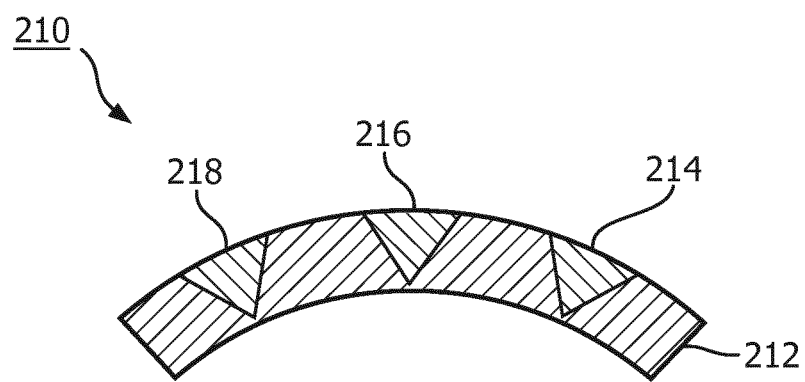
FIG. 8 is another section view of the support portion of FIG. 7, shown in a second configuration.

FIG. 7 shows a section view of another support portion (e.g., without limitation, sealing portion 210) in a first configuration and FIG. 8 shows a section view of sealing portion 210 in a second configuration. Sealing portion 210 includes a first portion 212 made of a first material having a first coefficient of thermal expansion and a number of other portions 214, 216, 218 made of materials having different coefficients of thermal expansion than the material of first portion 212. In this manner, sealing portion 210 moves between positions responsive to a change in environment (e.g., without limitation, temperature and/or humidity) in the same manner as sealing portions 10, 110, discussed above. However, as shown, portions 214, 216, 218 are generally triangular-shaped and extend substantially the entire way through first portion 212. As such, because the relatively thick upper portions (i.e., proximate the engaging surface) of portions 214, 216, 218 expand more than the relatively thin lower portions of portions 214, 216, 218, when sealing portion 210 is in the second configuration (FIG. 8), the engaging surface is relatively smooth. Furthermore, it is also within the scope of the disclosed concept for each of portions 214, 216, 218 to be made of a different material, advantageously allowing better control over the resultant shape of sealing portion 210 in the second configuration (FIG. 8). Accordingly, the size, shape, material, and/or dimensions of second portions 214, 216, 218 may be varied without departing from the scope of the disclosed concept.

Cushion members 2, 102 and a cushion including sealing portion 210 may be made by, for example and without limitation, a suitable method of three-dimensionally printing two different materials on one another, known as 4D printing. As such, a method of manufacturing a cushion member 2, 102 includes the steps of providing body portion 4, 104, providing first portion 12, 112, 212, and providing second portion 14, 16, 18, 114, 116, 118, 120, 214, 216, 218. The providing first portion 12, 112, 212 step may further include printing first portion 12,112,212 with a three-dimensional printer, and the providing second portion 14, 16, 18, 114, 116, 118, 120, 214, 216, 218 step may further include printing second portion 14, 16, 18, 114, 116, 118, 120, 214, 216, 218 with the three-dimensional printer. The providing second portion 14, 16, 18, 114, 116, 118, 120, 214, 216, 218 step may further include overmolding second portion 14, 16, 18, 114, 116, 118, 120, 214, 216, 218 on first portion 12, 112, 212. Accordingly, it will be appreciated that first portion 12, 112, 212 and second portion 14, 16, 18, 114, 116, 118, 120, 214, 216, 218 can either together, or in any combination, be provided by a suitable three-dimensional printing process or by an overmolding process.

Accordingly, it will be appreciated that the disclosed concept provides for an improved (e.g., without limitation, better able to seal against a face of a patient and thereby minimize the occurrence of leaks during therapy) cushion member 2, 102 and method of manufacturing the same, in which a support portion 10, 110, 210 changes shape responsive to a change in environment (e.g., without limitation, temperature and/or humidity).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A cushion member for a patient interface device, the cushion member comprising:
    a body portion comprising a first end and a second end disposed opposite the first end, the body portion defining a passage therethrough; and
    a support portion extending from the second end into the passage, the support portion comprising a first portion and a second portion disposed on or in the first portion, wherein the support portion is movable from a first configuration to a second configuration responsive to a change in environment, wherein the first portion is made of a first material having a first coefficient of thermal expansion, and wherein the second portion is made of a second material having a second coefficient of thermal expansion different than the first coefficient of thermal expansion, wherein the support portion has an engaging portion structured to engage a face of a user; wherein the engaging portion faces away from an interior of the body portion; wherein, when the support portion is in the first configuration, the engaging portion is generally smooth; and wherein, when the support portion is in the second configuration, the engaging portion is roughened.

2. The cushion member according to claim 1, wherein the first coefficient of thermal expansion is less than the second coefficient of thermal expansion; and wherein the second portion faces away from an interior of the body portion.

3. The cushion member according to claim 1, wherein the difference between the first coefficient of thermal expansion and the second coefficient of thermal expansion is a first number; wherein the average of the first coefficient of thermal expansion and the second coefficient of thermal expansion is a second number; and wherein the first number divided by the second number is greater than 0.10.

4. The cushion member according to claim 1, wherein the first portion has a nose bridge region, a first cheek region, and a second cheek region; wherein the support portion further comprises a third portion and a fourth portion each being made of a material having a coefficient of thermal expansion different than the first coefficient of thermal expansion; wherein the second portion is disposed on the first cheek region; wherein the third portion is disposed on the nose bridge region; and wherein the fourth portion is disposed on the second cheek region.

5. The cushion member according to claim 1, wherein the support portion has an inner edge portion; wherein the cushion member has a first center of curvature when the support portion is in the first configuration and a first radius of curvature extending from the first center of curvature to the inner edge portion; wherein the cushion member has a second center of curvature when the support portion is in the second configuration and a second radius of curvature extending from the second center of curvature to the inner edge portion; wherein the second center of curvature is closer to the support portion than the first center of curvature; and wherein the second radius of curvature is less than the first radius of curvature.

6. The cushion member according to claim 1, wherein the support portion is a sealing portion structured to engage a face of a user.

7. The cushion member according to claim 1, wherein the second portion at least partially extends into the first portion.

8. The cushion member according to claim 1, wherein the change in environment is selected from the group consisting of a change in temperature and a change in humidity.

9. The cushion member according to claim 1, wherein, when the support portion moves from the first configuration to the second configuration, the support portion moves in a predetermined manner in order to be more curved.

10. A method of manufacturing a cushion member for a patient interface device, the method comprising the steps of:
   providing a body portion having a first end and a second end disposed opposite the first end, the body portion defining a passage therethrough;
   providing a first portion of a support portion, the first portion extending from the second end into the passage; and
   providing a second portion of the support portion in or on the first portion, wherein the support portion is movable from a first configuration to a second configuration responsive to a change in environment, wherein the support portion changes shape when moving from the first configuration to the second configuration, wherein the first portion is made of a first material having a first coefficient of thermal expansion, and wherein the second portion is made of a second material having a second coefficient of thermal expansion different than the first coefficient of thermal expansion, wherein the support portion has an engaging portion structured to engage a face of a user; wherein the engaging portion faces away from an interior of the body portion; wherein, when the support portion is in the first configuration, the engaging portion is generally smooth; and wherein, when the support portion is in the second configuration, the engaging portion is roughened.

11. The method according to claim 10, wherein the providing the first portion step further comprises printing the first portion with a three-dimensional printer.

12. The method according to claim 11, wherein the providing the second portion step further comprises printing the second portion with the three-dimensional printer.

13. The method according to claim 10, wherein the providing the second portion step further comprises overmolding the second portion on the first portion.

* * * * *